(12) United States Patent
Karron et al.

(10) Patent No.: US 7,955,617 B2
(45) Date of Patent: Jun. 7, 2011

(54) TRAUMATIC BRAIN INJURY BIOMARKER DIAGNOSTIC

(75) Inventors: Daniel B. Karron, New York, NY (US); Robert D. Eisler, Mission Viejo, CA (US)

(73) Assignee: Alliant Techsystems Inc., Minneapolis, MN (US)

( * ) Notice: Subject to any disclaimer, the term of this patent is extended or adjusted under 35 U.S.C. 154(b) by 958 days.

(21) Appl. No.: 11/834,493

(22) Filed: Aug. 6, 2007

(65) Prior Publication Data

US 2009/0041830 A1 Feb. 12, 2009

(51) Int. Cl.
*A61K 9/68* (2006.01)

(52) U.S. Cl. .......................... 424/440; 424/400; 424/439

(58) Field of Classification Search .................. 424/1.11, 424/1.49, 1.65, 1.81, 1.85, 1.89, 9.1, 9.2, 424/9.3, 9.4, 9.5, 9.6, 9.7, 9.8, 400, 439, 440; 206/223, 569, 570

See application file for complete search history.

(56) References Cited

OTHER PUBLICATIONS

Salivary Diagnostics; American Scientist, vol. 96 (Copyright-Sigma Xi, The Scientific Research Society and other rightsholders), published 2008, pp. 37-43.

*Primary Examiner* — D. L Jones

(74) *Attorney, Agent, or Firm* — Vidas, Arrett & Steinkraus

(57) ABSTRACT

Blast Induced Traumatic Brain Injury or bTBI needs objective and subjective testing that can be made quickly in the field. Subjective tests using shapes, textures, tastes and odors as disposable, edible candies on a stick may be carried in a field kit. An objective test that employs a similar candy on a stick bearing antibodies bound to bioluminescent marker reads whether molecules believed to be released into the mouth from an injured brain are present if they bind to the specific antibody which may then be read.

7 Claims, 2 Drawing Sheets

FIG. 3

Read ALL instructions before performing test – Page 1 of 1

Silverman BLAST Traumatic Brain Injury Diagnostic Device (bTBI)

Instructions for bTBI Examination

1. Ask ambulatory patients to sit down at table otherwise ask patient to sit up
2. Put the sample diagnostic forms 2 feet in front of the patient on a table.
3. Ask patient not to touch the sample shapes
4. Have drinking water immediately available with or without a straw
5. Removable dental prosthesis should be removed during this test
6. Read the following instructions to the patient:

*I will ask you to match the shape of a small lollipop that I will put into your mouth with one of the shapes in front of you*

*Please roll the object between your tongue and the roof of your mouth*

*Please do not let the object touch your teeth or any other part of your mouth*

*The shape I will put into your mouth is the same as one of the shapes I have put in front of you*

*Please point to that shape*

*Please do not remove the form from your mouth. I will remove the lollipop from your mouth when you are ready*

7. Reverse of this form is a data sheet for collecting patient data as directed
8. Introduce the shape into the patients mouth (Prevent patient from seeing the shape of the form)
9. Have patient identify the shape in their mouth by pointing to a shape on the table
10. Remove shape from patient's mouth without letting them see it
11. Have patient sip some water and swallow it before proceeding with the next shape
12. Repeat from step 8 to 11 for each trial
13. Exam is concluded. Do not discuss results with patient

Read ALL instructions before performing test – Page 1 of 1

TRAUMATIC BRAIN INJURY BIOMARKER DIAGNOSTIC

CROSS-REFERENCE TO RELATED APPLICATIONS

None.

STATEMENT REGARDING FEDERALLY SPONSORED RESEARCH OR DEVELOPMENT

Not Applicable.

FIELD OF THE INVENTION

This invention relates to the diagnosis of traumatic brain injury (TBI), either of blast and impact etiology (caused) and a kit for detection of such injuries in the field. In particular, the invention is useful in diagnosing blast induced traumatic brain injuries (bTBI).

BACKGROUND OF THE INVENTION

Traumatic Brain Injury (TBI) can be caused by impact or blast shock waves. TBI in the civilian population is generally due to car crashes, where an unrestrained (no seatbelt) person's head impacts the windshield. This causes brain contusion, hematoma, diffuse axonal injury, ischemia, and a host of other injury catabolic cascade products. Impact TBI brain injuries have localized bruising and a more obvious area of the injury. Recently, combat injuries are being seen in which field armor has protected the patient well enough that the traumatic brain injuries tend to be from the force of the blast wave itself. Such damage, termed here as blast Traumatic Brain Injuries or bTBI have more subtle, but widespread diffuse axonal brain tissue damage that is more difficult to assess. Currently, bTBI is diagnosed by a diagnostic interview conducted by an experienced neurointensivist or psychologist with special training. This is a subjective diagnosis rendered by a clinician.

There is a need for both an objective and subjective field test to assess the bTBI quickly so the patients can be quickly triaged and treated appropriately. Presently, a key diagnostic for bTBI is whether the patient has been in a blast but doesn't remember the blast. This lack of continuity in the patient's consciousness is called syncope. It is similar to a faint, only with a more powerful exogenous precipitating cause. In the literature, it has been termed as a 'rebooting' of the brain after a traumatic halting of all mental processes.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF SUMMARY OF THE INVENTION

A diagnostic device for assessing brain injury, comprises a candy lollypop carried on a disposable stick; the candy lollypop includes an antibody to a biomarker for brain damage, bound to a bioluminescence compound.

A field test kit for assessing possible brain injury may comprise a disposable lollypop consisting of a candy on a stick in a stereoagnosis form; a disposable lollypop consisting of a candy on a stick with a defined taste incorporated therein; a disposable lollypop consisting of a candy on a stick with a defined smell incorporated therein; a disposable lollypop consisting of a candy on a stick with an antibody to a biomarker for brain damage bound to a bioluminescence compound; and instructions regarding the use of the lollypop tests.

BRIEF DESCRIPTION OF THE DRAWINGS

A detailed description of the invention is hereafter described with specific reference being made to the drawings in which:

FIG. 3 is a mockup of an instruction sheet to be placed within the field kit;

DETAILED DESCRIPTION OF THE INVENTION

Figure 1:
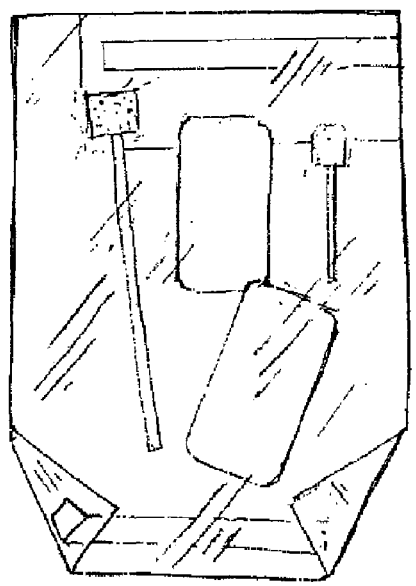
FIG. 1 is a mockup of a field kit in a sterile plastic bag containing the testing lollypops.

Both subjective and objective tests have been developed to help diagnose whether blast induced traumatic brain injury (bTBI) has occurred in the blast exposed military or civilian personnel using a field test kit that may be used by field medics to quickly triage a patient.

bTBI are Signature Wounds of the Iraq Conflict. Due to the increases protection of the body by using body armor, victims are surviving explosions which previously were fatal. These blasts are causing different classes of damage from typical civilian impact brain damage. They are believed to cause less localized damage and more widespread, yet subtle damage that is often masked by other trauma, such as diffuse axonal injury and channelopathies (damage to axonal ion channels and pumps).

1. bTBI represents diffuse injury to brain (no focal lesion) and associated with blast wave exposure from IEDs (Improvised Explosive Devices) and other explosive events 2. Moderate and severe blast exposures causing bTBI are obscured by polytrauma and casualty does not remember event which complicates diagnosis 3. For mild exposures representing significant percentage of bTBI cases, there is no evidence of wound however casualty manifests cognitive, motor, and personality deficits which may not become apparent until chronic phase of bTBI 4. Blast effects are cumulative so that repeated subthreshold/subclincial exposures can eventually result in bTBI 5. Currently diagnosed in chronic stage months after exposure using battery of neurocognitive testing 6. Better and objective bTBI diagnosis needed ASAP so that casualty can be triaged to appropriate echelon of care and remedial treatment initiated while in acute phase It is believed that bTBI involves damage to cranial nerves and that the damage may be directly measured by stimulating nerves which may have been damaged. Taste, smell and Stereoagnosis may be tested.

The invention provides objective and subjective testing for bTBI that can be in a field kit form easily used in the field by a medic to quickly assess the extent of the bTBI.

In Stereoagnosis, the damage in the parietal lobe is opposite to the side of the body where they cannot identify objects with touch. A person with Stereoagnosis cannot identify objects in their mouth or hands. A field kit containing a set of sample shapes attached to hand held sticks can be used to help assess whether bTBI has occurred. If the patient has difficulty identifying the shapes in their mouth it is diagnostic of bTBI as well as concomitant facial or trigeminal nerve damage.

The test shapes are of different sizes and textures. In addition, the shapes on sticks may test ability to identify taste, such as sweet, salty, bitter and sour. Damage to facial nerves may be indicated by inability to distinguish tastes.

The kit may also include shapes on sticks that test for sense of smell, such as pungent or rose smells. TBI induced damage to the olfactory bulb and brain can be evaluated with these test stimuli.

The Stereoagnosis diagnostic shapes may be cast in the required shapes from metal or other material that may be readily cleaned and disinfected and preferably includes a molded handle which may be held by the patient or the tester. The taste and smell forms are preferably disposable, and may include a common candy base molded into a Stereoagnosis form that additionally carries the different tastes or smells to be tested. In such forms, a simple stick such as in conventional candies on a stick may be used, such as a wood or rolled paper handle.

In these forms, the field kit includes completely disposable testing "lollypops" which are each inserted into the patient's mouth for assessment of their possible bTBI. In addition, the field kit preferably includes completely objective test lollypops that include specific antibodies that bind to chemicals released into the mouth due to bTBI. The released chemicals bind to the fluorophore moiety on the lollypop surface. This consists of bioluminescent chemicals bound to the antibodies. These TBI biomarkers can then bind to fluorophores and their concentration measured in picomolar or single molecule concentrations. The presence of bTBI may thus be assessed using traditional photon detector machines which provide extremely accurate counts of the brain catabolic by-products.

Objective measures may be assessed using testing of the three special sensory cranial nerves in subjects after traumatic brain injury.

1. The Olfactory nerve, a pure sensory nerve which perceives a sense of smell.
2. Optic nerve, a pure sensory nerve which perceives the sense of vision.
3. Trigeminal nerve, a mixed general motor and general sensory nerve, one part of which perceives the general sense of stereoagnosis which is the ability to perceive the size, shape and texture of 3 dimensional forms in the mouth.

The above objective tests can also be correlated with 3 other sensory tests of visual field, vestibular or balance (as in the Romberg effect) and acoustic sound localization.

Stereoagnosis forms are a battery of 10 discrete forms such as rectilinear and curvilinear shapes with smooth or textured forms attached to a four inch handle. Stereoagnosis was developed by Dr. Sidney Silverman using discrete forms that are molded into defined shapes of surgical stainless steel that may be placed in the mouth.

Forms can be fabricated from cast metal (Cobalt Chrome), plastic resins (Methyl Methacrylate) or cast hard candy base. Shapes will range from 4 to 8 mm in diameter and will be constructed as cubes, spheres and ovoid forms. Each of these 3 forms will be in 3 sizes so patient can differentiate size relationships. One of the forms will be 50 percent smaller the middle form and one will be 50 percent larger then middle form.

Other forms such as a cube or an oblong with one surface serrated and the rest will be smooth. Forms used for the test will have large size version duplicates (made out of plastic resin) of the forms placed in the mouth which will be 10× larger so the patient will be able to visually identify this form with the forms placed in the patient's mouth.

1) For shape identification, 1 rectilinear (not cubes), 1 spheres, 1 ovoid, 1 cube, 1 mixed ovoid/rectilinear form (One side would be round and another would be rectilinear).

2) For texture, 1 rectilinear, 1 sphere, 1 ovoid, 1 cube, 1 mixed ovoid/rectilinear form.

3) Each of the above forms should be a duplicate 50% larger then the mean size and another duplicated 50% smaller then the mean size.

4) Each of the 10 forms listed above in 1 & 2 will also have an enlarged form for visual display and identification by patient.

Thus there will be 30 forms for oral identification and 10 forms for visual identification. At no time should the subject see the forms placed or removed from the mouth, touch the forms or replicas of forms with fingers or place the forms between teeth to facilitate identification.

Gustatory function will be tested using a similar size stick as for the Stereoagnosis forms (a "lollipop") with flavors for sweet, sour, bitter and salty of differing concentrations. Smell will be tested with standard University of Pennsylvania Smell Test (UPSIT) and also assorted scratch'n'sniff paper tests.

The above tests can also be correlated with 3 other sensory tests of visual field, vestibular or balance (as in the Romberg effect) and acoustic sound localization which would then provide complete coverage of all special sensory cranial nerves.

Known 3D Stereoagnosis forms onto steel or paper stick handles to make it easier for the diagnostician to handle and put in and take out of the patients' mouth. Further, it makes it harder for the patient to accidentally swallow. These known forms have different shapes, sizes and textures.

The known 3D stereoagnosis forms may also be formed into candy, and placing the candy onto a disposable stick/handle, and adding smell and taste tests to the shape, size and texture tests. The forms may now be made edible/disposable with no need for cleaning and autoclaving since there is no reuse. The lollypops may be formed as conventional hard candies, preferably neutral in taste except for forms in which taste is to be tested.

1) Handles on the stereognositic forms to make it easier for patient to handle and harder to swallow.
2) Make forms out of candy and place on a disposable handle/stick.
3) Added taste component to forms.
4) Combining all the above results with smell tests
5) Place all disposable/eatable forms into an autoclaved, vacuum sealed field kit with instructions for use enclosed, suitable for use by a field medic.

It is believed that damaged brains release chemicals into the extra-cellular space. Traumatic brain injury causes conduction failure, dumping of glutamate extra cellularly as well as small polypeptides and other brain catabolic by-products. These "biomarkers" are tested for by using diagnostic lollypops that have bioluminescent antibodies in the candy which glow when biomarker brain injury metabolites are present in the saliva. The lollypops are carefully bagged and taken to a commercially available biomedical detector that reads the photons released. Such systems can detect extremely low levels of the biomarkers that were in the saliva of the patient.

In this form, the patient is not required to provide any feed-back and the test is completely objective. A typical bioluminescent compound that may be employed is luciferine/luciferase which is readily available and may be safely used in many applications. Luciferase, when reduced is bioluminescent (the reaction chain shown is described in greater detail in Wienhausen and DeLuca (1982) Anal. Biochem. 127, 380, and Hastings et al. U.S. Pat. No. 4,278,761, hereby incorporated by reference. Other bioluminescent compounds may be used so long as they may be tolerated by the body in low concentrations.

Figure 2:
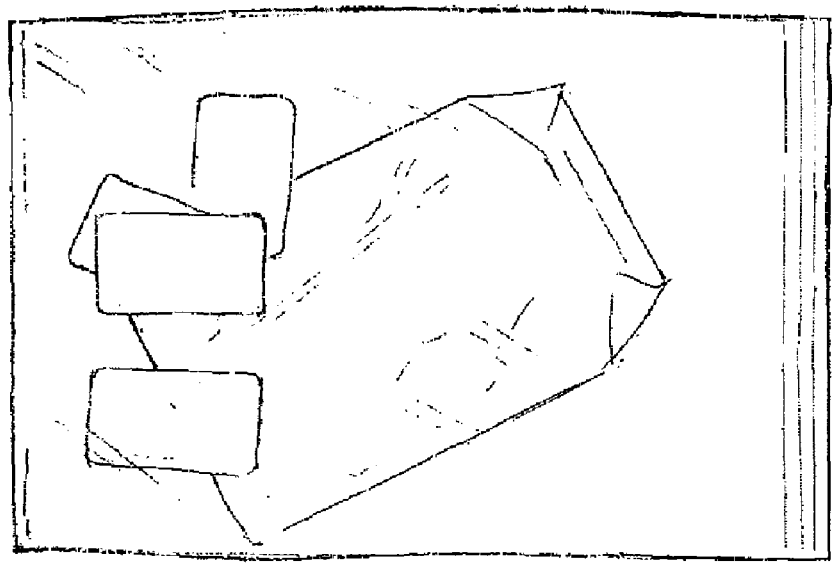
FIG. 2 is another view of the field kit of FIG. 1 showing lollypops of the invention.

Field Kit for subjective and objective evaluation of bTBI:
Field Kit is bTBI Acute Phase Diagnostic The field kit as shown in FIGS. 1 and 2 as a prototype is a collection of the various lollypops, which may include subjective and objective diagnostic lollypops in a sealed, sterile bag containing field instructions as shown in FIG. 3.

1. Subjective Diagnostic
   A. Patient self-reporting (see field pack instructions—FIG. 3).
      i. Shape in Mouth (Cube, Sphere, Heart): Inability to distinguish shape indicate damage to Cranial nerves 5 (Trigeminal) and 7 (Facial).
      ii. Taste (sweet, salty, bitter, sour): Inability to distinguish taste indicate damage to Cranial nerves 7 (Facial Nerve).
      iii. Smell (pungent, rose): Inability to distinguish smell indicates Cranial nerve 1 (Olfactory Nerve) trauma.
2. Objective Diagnostic
   A. Biophotonic detection (luciferin antibody glows in response to glutamate and other endotoxins).
      i. Small polypeptides released from nerve tissue injury metabolism (catabolism).
      ii. Luciferin based antibodies glow in the presence of brain catabolic by-products.

The field kit may be used for a single patient by a medic or other qualified personnel to assess the possible bTBI for the patient. They would take down the information for passing to physicians at a later time in addition to using their field results to triage the patient. The objective diagnostics requires biophotonic detection after the appropriate lollypops have been inserted into a patient's mouth.

The brain injury diagnosis of this invention has been noted with regard to bTBI. However, it may also be used to track biomarkers released in connection with other brain conditions including stroke and dementia.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A diagnostic device for assessing brain injury, comprising:
   a) a candy lollypop consisting of candy on a disposable stick;
   b) the candy lollypop including an antibody to a biomarker for brain damage, said biomarker being glutamate, bound to the bioluminescence compound luciferin.

2. The diagnostic device of claim 1, wherein the candy lollypop is made in a stereoagnosis form for assessing damage to the facial or trigeminal nerve.

3. The diagnostic device of claim 1, wherein the candy lollypop includes a defined taste selected from the group consisting of sweet, salty, bitter and sour, for assessing damage to the facial nerve.

4. The diagnostic device of claim 1, wherein the candy lollypop includes a defined smell for assessing damage to the olfactory nerve.

5. A field test kit for assessing possible brain injury including:
   a) a disposable lollypop consisting of a candy on a stick in a stereoagnosis form;
   b) a disposable lollypop consisting of a candy on a stick with a defined taste selected from the group consisting of sweet, salty, bitter and sour incorporated therein;
   c) a disposable lollypop consisting of a candy on a stick with a defined smell incorporated therein;
   d) a disposable lollypop consisting of a candy on a stick with an antibody to the biomarker for brain damage glutamate bound to a bioluminescence compound; and
   e) instructions regarding the use of the lollypop tests.

6. A field test kit for assessing possible brain injury comprising:
   a) a disposable lollypop consisting of a candy on a stick with an antibody to the biomarker for brain damage glutamate bound to a bioluminescence compound; and
   b) instructions regarding the use of the lollypop test.

7. The field kit of claim 6 wherein said bioluminescence compound is a luciferin.

* * * * *